United States Patent
Maruyama et al.

[11] 3,965,106
[45] June 22, 1976

[54] 3-PHENOXYPROPYLAMINE DERIVATIVES

[75] Inventors: Isamu Maruyama, Minoo; Masaru Nakao, Osaka; Kikuo Sasajima, Toyonaka; Shigeho Inaba, Takarazuka; Hisao Yamamoto, Nishinomiya, all of Japan

[73] Assignee: Sumitomo Chemical Company, Limited, Japan

[22] Filed: Dec. 12, 1973

[21] Appl. No.: 423,981

[52] U.S. Cl............ 260/293.83; 260/268 PH; 424/250; 424/267
[51] Int. Cl.² .................................. C07D 211/52
[58] Field of Search .............. 260/293.82, 293.83

[56] References Cited
UNITED STATES PATENTS

| | | | |
|---|---|---|---|
| 2,960,507 | 11/1960 | Stern et al. | 260/294.7 |
| 3,862,158 | 1/1975 | Edenhofer et al. | 260/293.77 |

*Primary Examiner*—G. Thomas Todd
*Attorney, Agent, or Firm*—Craig & Antonelli

[57] ABSTRACT

A 3-phenoxypropylamine derivative of the formula:

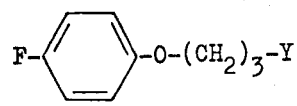

wherein Y is

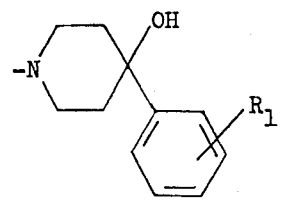

(wherein $R_1$ is a halogen atom or a trifluoromethyl group) or

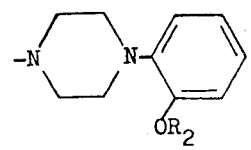

(wherein $R_2$ is a lower alkyl group) and its pharmaceutically acceptable salts which are useful as central nervous system depressing agents.

6 Claims, No Drawings

3-PHENOXYPROPYLAMINE DERIVATIVES

The present invention relates to novel 3-phenoxypropylamine derivatives and their pharmaceutically acceptable salts thereof, pharmaceutical compositions containing them and methods for their preparation.

The novel 3-phenoxypropylamine derivatives of this invention are represented by the formula:

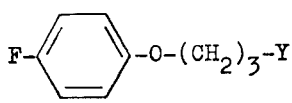  [I]

wherein Y is

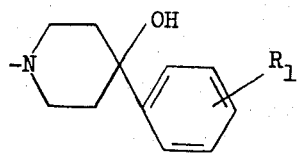

(wherein $R_1$ is a halogen atom or a trifluoromethyl group) or

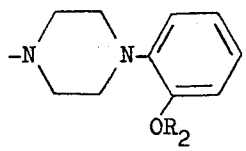

(wherein $R_2$ is a lower alkyl group).

As used herein, the term "halogen" includes fluorine, chlorine, bromine and iodine. The term "lower alkyl" includes alkyls having not more than 8 carbon atoms such as methyl, ethyl, n-propyl, iso-propyl, n-butyl, tert-butyl, n-pentyl and n-hexyl.

The 3-phenoxypropylamine derivatives [I] form pharmaceutically acceptable salts with a variety of inorganic and organic acids such as sulfuric, phosphoric, hydrochloric, hydrobromic, nitric, oxalic, malonic, succinic, lactic, tartaric, maleic, fumaric, formic, acetic and p-toluenesulfonic acids.

The 3-phenoxypropylamine derivatives [I] and their pharmaceutically acceptable salts have valuable pharmaceutical properties. For instance, they show depressant activity of the central nervous system such as antiapomorphine activity and are useful as neuroleptic agents. The 3-phenoxypropylamine derivatives [I] and their pharmaceutically acceptable salts can be administered orally in conventional dosage forms such as tablet, capsule, solution, suspension or the like. A typical tablet may be constituted from 1 to 20 % by weight of a binder (e.g. tragacanth), from 1 to 20 % by weight of a lubricant (e.g. calcium stearate, magnesium stearate), an average dose of the active ingredient and q.s. 100 % by weight of a filler (e.g. lactose). The usual oral dosage of the active ingredient is 1 to 500 mg per day.

Accordingly, a basic object of the present invention is to provide novel 3-phenoxypropylamine derivatives [I] and their pharmaceutically acceptable salts which have excellent phamaceutical properties. Another object of this invention is to provide a process for producing novel and useful 3-phenoxypropylamine derivatives [I] and their salts. A further object of the invention is to provide pharmaceutical compositions containing novel and useful 3-phenoxypropylamine derivatives [I] or their salts. These and other objects of the invention will be apparent from the following descriptions.

According to the present invention, the 3-phenoxypropylamine derivatives [I] can be prepared by reacting a compound of the formula:

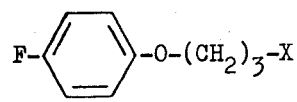  [II]

wherein X is a halogen atom (preferably chlorine, bromine or iodine) with a compound of the formula:

  [III]

wherein Y is as defined above.

The reaction may be carried out at a temperature ranging from about room temperature to the boiling point of the solvent used in the absence or presence of an acid acceptor in an inert organic solvent such as benzene, toluene, xylene, dimethylformamide, pyridine, methanol, ethanol or a mixture thereof. Suitable acid acceptors include sodium carbonate, potassium carbonate, sodium bicarbonate, potassium bicarbonate, sodium hydroxide, potassium hydroxide, sodium hydride, potassium hydride, triethylamine and the like.

The 3-phenoxypropylamine derivatives [I] can be also prepared by reducing a compound of the formula:

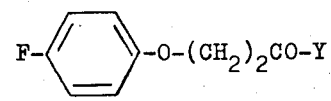  [IV]

wherein Y is as defined above with a reducing agent such as lithium aluminium hydride. The reduction may be carried out at a temperature below room temperature, at room temperature or at an elevated temperature in the presence of a solvent or solvent mixture. Suitable solvents include ether, tetrahydrofuran, dioxane, N-ethylmorpholine and the like.

The compounds of the formula [IV] can be easily prepared in a conventional procedure according to the following reaction scheme:

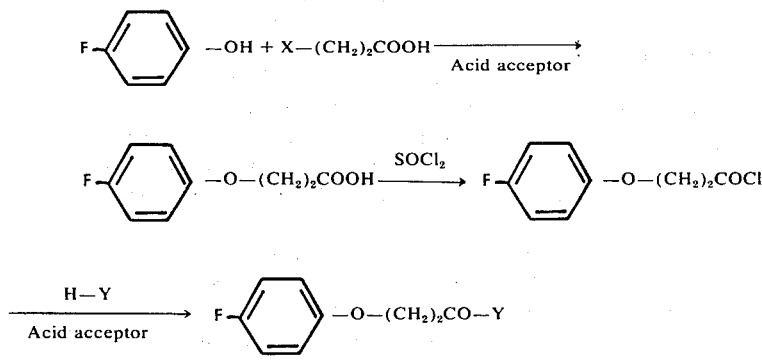

wherein Y and X are as defined above.

The present invention is further disclosed in the following Examples of more preferred embodiments thereof, which are presented for the purpose of illustration and it is not intended to limit the scope of the invention.

EXAMPLE 1

A mixture of 2.83 g of 1-chloro-3-(p-fluorophenoxy)-propane, 3.18 g of 4-(p-chlorophenyl)-4-hydroxypiperidine, 0.8 g of sodium carbonate and 60 ml of dimethylformamide is heated at a temperature of 80° – 90°C for 10 hours. After cooling, the reaction mixture is poured into water. The precipitate is collected by filtration and dried to give 1-[3-(p-fluorophenoxy)-propyl]-4-(p-chlorophenyl)-4-hydroxypiperidine, M.P. 134 – 135°C. Recrystallization from benzene gives the purified product, M.P. 136° – 137°C.

The following compounds are obtained in the same manner as in Example 1:

1-[3-(p-Fluorophenoxy)propyl]-4-(p-fluorophenyl)-4-hydroxypiperidine hydrochloride, M.P. 184° – 185°C.

1-[3-(p-Fluorophenoxy)propyl]-4-hydroxy-4-(m-trifluoromethylphenyl)piperidine hydrochloride, M.P. 184° – 184.5°C.

1-[3-(p-Fluorophenoxy)propyl]-4-(o-methoxyphenyl)-piperazine dihydrochloride, M.P. 189°–190°C (decomp.).

1-[3-(p-Fluorophenoxy)propyl]-4-(o-ethoxyphenyl)-piperazine, M.P. 108° – 109°C.

1-[3-(p-Fluorophenoxy)propyl]-4-(o-n-propoxyphenyl)-piperazine, M.P. 78° - 78.5°C.

EXAMPLE 2

To a mixture of 0.4 g of lithium aluminium hydride and 20 ml of tetrahydrofuran is added dropwise a solution of 1.8 g of 1-[3-(p-fluorophenoxy)propionyl]-4-(o-methoxyphenyl)-piperazine in tetrahydrofuran under cooling. Then, the resulting mixture is refluxed for 3 hours. To the reaction mixture cooled in ice, there are gradually added water and benzene. The organic layer is separated, washed with water, dried over sodium sulfate and evaporated under reduced pressure. The oily residue is dissolved in ether and treated with ethanolic hydrogen chloride under cooling. The precipitate is collected by filtration and dried to give 1-[3-(p-fluorophenoxy)propyl]-4-(o-methoxyphenyl)piperazine dihydrochloride, M.P. 187° – 189°C (decomp.). Recrystallization from ethanol gives the purified product, M.P. 189° – 190°C (decomp.).

What is claimed is:

1. A 3-phenoxypropylamine derivative of the formula:

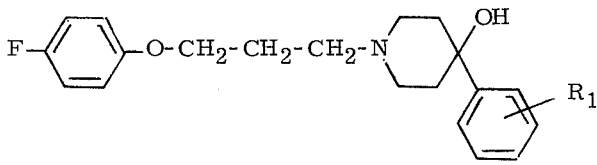

wherein $R_1$ is a halogen atom or a trifluoromethyl group.

2. The 3-phenoxypropylamine derivative according to claim 1, wherein $R_1$ is a halogen atom.

3. The 3-phenoxypropylamine derivative according to claim 1, wherein $R_1$ is a trifluoromethyl group.

4. A pharmaceutically acceptable salt of the 3-phenoxypropylamine derivative according to claim 1.

5. 1-[3-(p-Fluorophenoxy)propyl]-4-(p-chlorophenyl)-4-hydroxypiperidine or its pharmaceutically acceptable salt.

6. 1-[3-(p-Fluorophenoxy)propyl]-4-hydroxy-4-(m-trifluoromethylphenyl)piperidine or its pharmaceutically acceptable salt.

* * * * *

UNITED STATES PATENT OFFICE
CERTIFICATE OF CORRECTION

Patent No. 3,965,106            Dated     June 22, 1976

Inventor(s) Isamu Maruyama, Masaru Nakao, Kikuo Sasajima, Shigeho Inaba, and Hisao Yamamoto It is certified that error appears in the above-identified patent and that said Letters Patent are hereby corrected as shown below:

Title page, first column, insert as new paragraph after line 10:

-- Foreign Application Priority Data

December 22, 1972      Japan . . . . . . . 2276/72 --

Signed and Sealed this

Twenty-sixth Day of October 1976

[SEAL]

Attest:

RUTH C. MASON
*Attesting Officer*

C. MARSHALL DANN
*Commissioner of Patents and Trademarks*